United States Patent [19]

Chu et al.

[11] E Patent Number: Re. 33,405

[45] Reissued Date of Patent: Oct. 23, 1990

[54] PURIFIED HUMAN PROSTATE ANTIGEN

[75] Inventors: Tsann M. Chu; Ming C. Wang, both of Williamsville; Lawrence Papsidero, Lakawanna, all of N.Y.

[73] Assignee: Research Corporation Technologies, Inc., Tuscon, Ariz.

[21] Appl. No.: 254,015

[22] Filed: Oct. 4, 1988

Related U.S. Patent Documents

Reissue of:

[64] Patent No.: 4,446,122
Issued: May 1, 1984
Appl. No.: 316,954
Filed: Dec. 23, 1980

U.S. Applications:

[63] Continuation-in-part of Ser. No. 108,217, Dec. 28, 1979, abandoned.

[51] Int. Cl.[5] ..... G01N 33/536; C12P 21/08; C07K 15/28; C07K 15/06

[52] U.S. Cl. ..... 530/350; 530/380; 530/387; 530/395; 530/808; 530/809; 530/821; 530/850; 435/7; 435/172.2; 435/240.27; 436/536; 436/538; 436/542

[58] Field of Search ..... 530/350, 380, 395, 387, 530/808, 809, 821; 435/7, 240.27, 172.2; 424/85.8; 436/536, 538, 542

[56] References Cited

U.S. PATENT DOCUMENTS 4,172,124 10/1979 Koprowski et al. .
4,331,647 5/1982 Goldenberg ..... 424/1

OTHER PUBLICATIONS

Kohler et al, *Nature,* 256, pp. 495–497 (1975).
Papsidero, L. D. et al., Progress in Clinical and Biological Research, vol. 75A, pp. 435–443 (1981).
Wang, M. C. et al., The Prostate, vol. 2, pp. 89–96 (1981).
Shulman, A. et al., Proc. Society for Experimental Biology and Medicine, vol. 137 (1), pp. 97–100 (1971).
Papsidero, L. D. et al., J. National Cancer Institute, vol. 66 (1), pp. 37–42 (1981).
Kuriyama, T. et al., Cancer Research, vol. 41 (10), pp. 3874–3876 (1981).
Clark, S. M. et al., Medical and Pediatric Oncology, vol. 9 (1), p. 94 (1981).
Wang et al., Investigative Urology, vol. 17, No. 2, pp. 159–163 (1979).
Chemical Abstracts, vol. 87, issued 1977, Abstract No. 163812b, Heyns.
Chemical Abstracts, vol. 82, issued 1975, Abstract No. 123206x, Brannen et al.
Nature, vol. 266, issued Apr. 7, 1977, p. 495, Welsh.
Nature, vol. 272, issued Apr. 27, 1978, pp. 751–752, Simpson.
Proc. Natl. Acad. Sci. USA, vol. 74, No. 7, pp. 2958–2988, Jul. 1977, Koprowski et al.
Proc. Natl. Acad. Sci. USA, vol. 76, No. 3, pp. 1438–1442, Mar. 1979, Herlyn et al.
Proc. Natl. Acad. Sci USA, vol. 77, No. 1, pp. 563–566, Jan. 1980, Accolla et al.
Barnes, Fed. Amer. Soc. Expt. Biol. Abstracts of the 50th Annual Meeting, Atlantic City, NJ, Apr. 11–16, 1966, Abstract No. 932.
Hara, M., Koyanagi, Y., Inoue, T., Fukuyama, T., Some Physico–Chemical Characteristics of Gamma–Seminoprotein, an Antigenic Component Specific for Human Seminal Plasma, Jpn J. Leg Med, 1971; 25:322–4.
Hara, Forensic Immunological Studies on Human Body Fluids, 28 NIPPO ISHI 3, 164–176 (1974).
Tsuda et al., Study of Heterogeneity of Gamma–Seminoprotein on Polyacrylamide Gel Electrophoresis (II) and (III), 33 NIPPON ISHI 2, 132–138 (1979).
Koyanagi, Yoshiko, On the Preparation, Chemical Analysis and Some Physico–Chemical Characterization of "gamma seminoprotein", an Antigenic Component Specific for Human Seminal Plasma, Journal title in Japanese, pp. 87(547), 88(548).
Li, T. S., Beling, C. G., Isolation and Characterization of Two Specific Antigens of Human Seminal Plasma, Fertil. Steril., 1973:24:134–44.
Li, T. S. and Shulman, S., Immunoelectrophoretic Analysis of Human Seminal Plasma Fractions after Fractionation by Various Methods, International Journal of Fertility, vol. 16, No. 2, 1971, pp. 87–100.
Sensabaugh, G. F., Isolation and Characterization of a Semen–Specific Protein from Human Seminal Plasma: A Potential New Marker for Semen Identification, J. Forensic Sci., 1978; 23:106–18.
Graves, Howard G. B. et al., Postcoital Detection of Male–Specific Semen Protein, The New England Journal of Medicine, vol. 312, No. 6, pp. 338–343 (1985).
Hou Yiping, Wu Meiyun, Isolation and Purification of p30 from Human Seminal Plasma, J. West China Univ. Med. Sci., 18(4), 1987, 357–360.

*Primary Examiner*—Margaret Moskowitz
*Assistant Examiner*—Jeff Kushan
*Attorney, Agent, or Firm*—Scully, Scott, Murphy & Presser

[57] ABSTRACT

A prostate antigen distinct from prostatic acid phosphatase has been detected in normal, benign hypertrophic and malignant prostatic tissues, but not in other human tissues. The prostate antigen was purified to homogeneity from prostatic tissues by ammonium sulfate precipitation, DEAE-BioGel A anion exchange chromatography, molecular sievings on Sephadex G-100 and Sephadex G-75, and preparative polyacrylamide gel electrophoresis. The purified prostate antigen shows a single protein band on analytical polyacrylamide gel electrophoresis and isoelectric focusing. The molecular weight of purified antigen was estimated by Sephadex G-75 gel filtration to be 33,000 and by sodium dodecyl sulfate polyacrylamide gel electrophoresis to be 34,000 with no subunit. The prostate antigen had an isoelectric point of 6.9.

32 Claims, No Drawings

PURIFIED HUMAN PROSTATE ANTIGEN

Matter enclosed in heavy brackets [ ] appears in the original patent but forms no part of this reissue specification; matter printed in italics indicates the additions made by reissue.

This invention was supported in part by Grants No. CA-15126 and CA-15437 from the National Cancer Institute, U.S. Public Health Service.

DESCRIPTION OF THE INVENTION

This application is a continuation-in-part of copending, commonly assigned U.S. patent application Ser. No. 108,217 now abandoned, filed Dec. 28, 1979, the contents of which are incorporated by reference herein.

TECHNICAL FIELD OF THE INVENTION

This invention relates to a diagnostic reagent and method for the immunochemical detection of a human prostate antigen which is distinct from prostatic acid phosphatase. More particularly, this invention relates to a novel purified human prostate antigen and antibodies specific thereto which are suitable for use in prostatic cancer detection by laboratory methods.

BACKGROUND ART

Prostate cancer is very prevalent in old age, with approximately one half of all males over age 70 having been shown to develop prostatic cancer. This high incidence of prostate malignancy had led to the search for markers which may be used for its detection. The elevation of serum acid phosphatase activity in patients having metastasized prostate carcinoma was first reported by Gutman et al. in J. Clin. Invest. 17: 473 (1938). In cancer of the prostate, prostatic acid phosphatase is released from the cancer tissue into the blood stream with the result that the total serum acid phosphatase level greatly increases above normal values. Numerous studies of this enzyme and its relation to prostatic cancer have been made since that time, e.g., see the review by Yam in Amer. J. Med. 56: 604 (1974). However, the measurement of serum acid phosphatase by conventional spectrophotometric methods often fails to detect prostatic cancer in its early stages. In general, the activity of serum acid phosphatase is elevated in about 65–90 percent of patients having carcinoma of the prostate with bone metastatis; in about 30 percent of patients without roentgenological evidence of bond metastasis; and in about only 5–10 percent of patients lacking clinically demonstrable metastasis.

Prior art attempts to develop a specific test for prostatic acid phosphatase have met with only limited success because techniques which rely on enzyme activity on a so-called "specific" substrate cannot take into account other biochemical and immunochemical differences among the many acid phosphatases which are unrelated to enzyme activity of prostate origin. In the case of isoenzymes, i.e. genetically defined enzymes having the same characteristic enzyme activity and a similar molecular structure but differing in amino acid sequences and/or content and therefore immunochemically distinguishable, it would appear inherently impossible to distinguish different isoenzyme forms merely by the choice of a particular substrate. It is therefore not surprising that none of these prior art methods is highly specific for the direct determination of prostatic acid phosphatase activity; e.g. see Cancer 5: 236 (1952); J. Lab. Clin Med. 82: 486 (1973); Clin. Chem. Acta. 44: 21 (1973); and J. Physiol. Chem. 356: 1775 (1975).

In addition to the aforementioned problems of nonspecificity which appear to be inherent in many of the prior art reagents employed for the detection of prostate acid phosphatase, there have been reports of elevated serum acid phosphatase associated with other diseases, which further complicates the problem of obtaining an accurate clinical diagnosis of prostatic cancer. For example, Tuchman et al. in Am. J. Med. 27: 959 (1959) have noted that serum acid phosphatase levels appear to be elevated in patients with Gaucher's disease.

Due to the inherent difficulties in developing a "specific" substrate for prostrate acid phosphatase, several researchers have developed immunochemical methods for the detection of prostate acid phosphatase. However, the previously reported immunochemical methods have drawbacks of their own which have precluded their widespread acceptance. For example, Shulman et al., in Immunology 93: 474 (1964) described an immunodiffusion test for the detection of human prostate acid phosphatase. Using anisera prepared from a prostatic fluid antigen obtained by rectal message from patients with prostatic disease, no cross-reactivity precipitin line was observed in the double diffusion technique against extracts of normal kidney, testicle, liver and lung. However, this method has the disadvantages of limited sensitivity, even with the large amounts of antigen employed, and of employing antisera which may cross-react with other, antigenically unrelated serum protein components present in prostatic fluid.

Chu et al. in International Patent Application Publication No. WO 79/00475, the contents of which are incorporated by reference herein, describe a new method for the detection of prostatic acid phosphatase isoenzyme patterns associated with prostatic cancer which obviates many of the above drawbacks. However, practical problems are posed by the need for a source of cancerous prostate tissue from which the diagnostically relevant prostatic acid phosphatase isoenzyme patterns associated with prostatic cancer are extracted for the preparation of antibodies thereto.

In recent years considerable effort has been spent to identify enzyme or antigen markers for various types of malignancies with the view towards developing specific diagnostic reagents. The ideal tumor marker would exhibit, among other characteristics, tissue or cell-type specificity, and would be released into the circulation or other biological milieu which is easily obtained from individuals. Previous investigators have demonstrated the occurrence of human prostate tissue-specific antigens.

For example, R. H. Flocks et al., I. J. Urol. 84: 134 (1960) immunized rabbits with an extract of BPH (benign prostatic hypertrophy) prostate tissue and showed the presence of tissue specific antiprostatic antibodies by a gel diffusion technique. However, they presented no data at all to indicate the nature of the reactive antigen. The precipitation lines formed by antiserum and prostate extract appear due to the reaction of prostatic acid phosphatase and its antibodies.

R. J. Ablin et al., J. Immunol. 104: 1329 (1970) and R. J. Ablin, Cancer 29: 1570 (1972) have also demonstrated the occurrence of human prostate tissue-specific antigens. By using antiserum obtained from immunizing rabbits with extracts of normal prostate, Ablin et al.

showed two antigenic components in human prostate. One of these was identified as prostatic acid phosphatase, while the specificity of other was shown to be a non-prostatic tissue antigen. The xenoantibodies reactive to the second antigen could not be abolished by treating the antiserum with human prostatic fluid. Furthermore, this antigen was shown to be deficient in benign and malignant prostatic tissues. In contradistinction, the in prostate antigen of the present invention is present in all prostate tissue, (normal, benign or malignant) in almost equal amounts. Further, it is detectable prostatic fluid and cultured human prostatic malignant cells and its medium as well. The Ablin articles describe absorption of antisera to the antigens described therein with prostatic fluid, after which a precipitin line was still detected. Absorption of antibodies against the present antigen with prostatic fluid gives no precipitin line, indicating that the present antigen is present in prostatic fluid while that of Ablin et al. is not.

C. W. Moncure et al., Cancer Chemother. Rep. 59: 105, (1975) also demonstrated the occurrence of a human prostate tissue-specific antigen preparation which does not bind to DEAE sepharose at pH 8.0, as does the antigen of the present invention. This characteristic most probably indicates a significant structural difference between the present protein and that of Moncure et al.

Thus, there is still a need for simple, reliable, sensitive and specific reagents and techniques to detect prostatic cancer with acceptable diagnostic accuracy and without the aforementioned difficulties of the prior art. The present invention fills such needs.

DISCLOSURE OF THE INVENTION

It is a general object of the present invention to provide a purified human prostate antigen useful in preparing an improved diagnostic reagent suitable for the immunochemically specific detection of circulating human prostate antigen in blood, urine or other body fluids.

Another object of the present invention is to provide rapid and simple, yet highly specific and sensitive, immunochemical techniques and reagents useful in the early detection of prostatic cancer.

A further object of this invention is to provide a new marker for monitorong prostatic cancer and the effectiveness of curative therapy therefor.

An additional object of this invention is to provide useful monoclonal antibodies to human prostate antigen.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a purified human prostate antigen which is distinct from a prostatic acid phosphatase.

In a second aspect, the present invention provides antisera which are highly specific to a purified human prostate antigen and which do not immunochemically cross-react with prostatic acid phosphatases or with acid phosphatases originating from other tissues.

In a third aspect of the present invention, there is provided an immunochemical method for the detection of prostatic cancer which exhibits high sensitivity, good specificity and substantially no false positive results for tumor other than the prostate.

In a fourth aspect, the present invention provides specific marker antibodies against human prostate antigen which are useful, e.g., as carriers for in vivo radioimmunodetection of prostate cancer and immunospecific chemotherapy of prostatic cancer.

According to the present invention, antigenic preparations from either normal or cancerous human prostate tissue, prostatic fluid, cultured human prostatic malignant cells or their media are purified to obtain a preparation consisting essentially of a human prostate antigen free of prostatic acid phosphatase. These antigenic preparations are employed for immunological vaccination and diagnostic procedures, particularly for immunoprecipitin testing.

Since immunological studies indicate that this antigen is present in normal, benign hypertrophic and neoplastic prostate, a pool of various prostate tissues can be used as a starting material for subsequent purification. Briefly, the prostate tissue is first extracted in aqueous media at 4° C. Although EDTA-PBS solution is conveniently used, saline, 3 M KCl or 0.01 percent (v/v) Tween 80 (but not 1 M perchloric acid) also can be used for extraction of the prostate antigen. The antigen is thus also distinguished from carcinoembryonic antigens by its sensitivity to perchloric acid.

After clarification of the homogenate by centrifugation and filtration, the supernatant from the crude tissue extract is subjected to ammonium sulfate fractionation. Ammonium sulfate concentration at 20–80 percent saturation almost quantitatively recovers the prostatic antigen from EDTA-PBS extracts, with the highest yield at 45–50 percent saturation. In order to avoid contamination by other proteins as much as possible, the precipitate is preferably collected between 35–55 percent saturation of ammonium sulfate, which contains approximately 70 percent of the total prostate antigen in the crude extract.

Human seminal plasma has been found to contain an antigen, reacting with rabbit anti-PA serum in double immunodiffusion, which forms a fused immunoprecipitin line with that of crude extract of prostatic tissue. This result revealed that presence of a protein, immunologically identical to the human prostate antigen (PA), in seminal plasma. Further study showed that all seminal plasma specimens examined contained a substantial amount of PA, ranged from 0.4 to 1.8 mg/ml, ($n=9$, mean$\pm$standard deviation$=0.71\pm0.42$). It is estimated that PA content in 20 to 30 ml of seminal plasma was equivalent to that in 100 g of prostatic tissue. The elution profile of PA in chromatographies is similar to that using prostatic tissue as source of the antigen. PA purified from seminal plasma and from prostatic tissue possesses an identical mobility and isoelectric point (pI $6.87\pm0.09$) as shown by polyacrylamide gel electrophoresis and isoelectric focusing, respectively. Both purified PA preparations exhibit a molecular weight of 33–34,000 as shown by Sephadex G-75 gel filtration. In addition, a line of identity was obtained in immunodiffusion when purified PA preparations reacted with anti-PA serum.

Since seminal plasma is more readily available than prostatic tissues and contains abundance of PA, it appears an ideal source for isolating PA. Using seminal plasma as the source of PA isolation also appears to have an advantage over the use of prostatic tissue. Firstly, the initial extraction step, which requires at least 4 hours, is eliminated. Secondly, at the initial stage of purification, handling a large volume of the tissue extract is avoided since 20 to 30 ml of seminal plasma is equivalent to 100 g of tissue in terms of PA content. Thirdly, seminal plasma contains less contaminating proteins and makes purification easier. For instance, hemoglobin in the tissue extract is precipitated concurrently with PA by ammonium sulfate at concentration greater than 50 percent saturation, and the removal of this hemoglobin in later steps of purification results in a reduction of the yield of final purified PA. Since seminal plasma contains less contaminating proteins, it is possible during fractional precipitation steps to recover a greater amount of PA by increasing the upper cut-off point of ammonium sulfate concentration to 75 percent saturation. A better recovery of PA in purified form is also achieved from seminal plasma.

DEAE-BioGel A anion exchange column effectively retains the prostate antigen and washing the column with tris-HCl buffer at pH 8.0 does not dissociate the antigen from the column. Elution of the antigen can be achieved with 18–78 mM of NaCl in the same buffer, followed by further purification by gel chromatography. The bulk of contaminating proteins in the PA preparation eluted from the DEAE column have a molecular weight greater than 45,000 and can accordingly be separated from PA (molecular weight: 33,000 to 34,000) by gel filtration on a Sephadex G-100 column.

An additional step can be carried out with anion exchange chromatography on a DEAE column using a pH gradient solution as the eluant. Two protein peaks were detected between fractions in the pH range of 7.6 to 6.7, which were shown to contain PA. Upon polyacrylamide gel electrophoresis, protein heterogeneity was seen in the first peak fractions, while the second peak fractions gave a single protein band. Therefore, for obtaining homogeneous PA, only second peak fractions were collected. At the end of theis elution, approximately 20 percent of total PA subjected to chromatography was still bound to the DEAE column. This can be recovered quantitatively by elution with 0.08 M NaCl, but protein heterogeneity in the eluted PA preparation was observed. An interesting observation has been made in the course of the above PA purification; the first peak fractions contained PA which possessed a pI different from that of the purified PA from the second peak fractions. Also, the PA retained by the DEAE column at the end of pH gradient elution exhibited a different pI. Similar observations have also been made in the purification of PA from seminal plasma, and treatment with neuraminidase has increased the pI of thse PA "isomers" to a higher pH range. It thus appears that the human prostate antigen of the present invention may exist in a number of different isomeric forms.

Preparative polyacrylamide gel electrophoresis of the partially purified antigen is effective in achieving a pure antigen preparation. Thus purified antigen is shown to be homogeneous by polyacrylamide gel electrophoresis with and without sodium dodecyl sulfate. It has a molecular weight of 33,000–34,000 with no subunit, and exhibits a single pI of 6.9.

Using immunoprecipitation and immunocytochemical techniques, PA has been shown to be a prostate gland epithelial marker protein. PA is localized in the epithelial lining of prostatic glands and ducts as well as in prostatic secretions and concretions, but not in epithelia of periurethral glands, seminal vesicles, vas deferens, urinary bladder transitional epithelium, prostatic urethra, glandular lining of vonBrunn's nests, or in testes. These observations suggest that the PA in the seminal plasma is of prostatic origin.

Data are now available to indicate the potential clinical application of PA in prostatic cancer. Quantitation of circulating PA, with a sensitivity of 0.1 ng/ml, has been achieved by an enzyme-immunoassay. PA is not detected in sera from normal females or female cancer patients, while sera from male patients with non-prostate cancer contain a similar range of PA as that of normal males. Patients with prostatic diseases have been shown to have elevated levels of circulating PA. Although no quantitative difference in PA levels is found between patients with benign prostatic hypertrophy and stage A of prostatic cancer, patients with other stages of prostatic cancer demonstrate significantly elevated PA levels, both quantitatively and qualitatively. With immunocyto- chemical procedures, all primary and secondary prostatic tumors examined reacted positively with anti-PA serum, whereas the tumors of non-prostatic origin did not react. These results, therefore, suggest an additional means for diagnosis of prostate cancer and for monitoring the efficacy of its treatment. Another possible application is the use of specific anti-PA antibodies in in vivo radioimmunodetection of prostate cancer, e.g. according to the method described by D. Pressman in Cancer Research 40: 2960 (1980), particularly the micro-metastasis which is so critical in staging and treatment. Immune-specific chemotherapy also is a potential area where much work can now be initiated with the availability of PA immunologic reagents, e.g. see T. Ghose et al. in J. Nat. Cancer Inst. 61: 657 (1978). Furthermore, the physiology of the prostate can be studied with the aid of this new marker for prostate gland epithelium.

In order to produce antisera which can be used to detect antigens in prostate tissues and fluids other than acid phosphatase, female rabbits have been injected with a purified prostate antigen isolated from prostate tissue. Sera is collected, heat inactivated and stored at −20° C. until use. After treatment with insolubilized normal human plasma proteins (antibodies to normal plasma constituents are removed by treatment of the antiserum with glutaraldehyde-insolubilized normal plasma obtained from normal male and female adults), the antiserum reacts specifically with prostate tissue extracts (43/43) using the techniques of double immunodifussion and rocket immunoelectro-phoresis. No immunological reactivity was observed against a battery of extracts prepared from tissues other than prostate. The prostate antigen from prostate tissue extracts was characterized by gel filtration chromatography (m.w. 30–40,000), isoelectric focusing (pI 6.9) and agarose electrophoresis ($M_R$ 0.2 relative to bovine serum albumin). The concentration of the prostate antigen was not significantly different among extracts prepared from normal, benign hypertropic and malignant prostatic tissues and the antigen exhibited no acid phosphatase enzyme activity as determined by histochemical staining procedures. Furthermore, its approximate molecular weight (30–40,000) differs significantly from that of prostatic acid phosphatase (100,000).

Although the antigen detected in serum had a higher apparent molecular weight (80–100,000), antigen mixing and peak enhancement experiments indicate that prostate antigen in circulation is immunologically identical to the human prostate antigen in prostate tissue and prostatic fluid. The serum-borne antigen may be bound to a plasma protein. Such plasma protein binding of a variety of antigens and hormonal substances is well known and has been reported by T. Peters, Jr. "Serum Albumin" In: F. W. Putman (ed.). The Plasma Proteins. Vol. 1: pp. 133–153, New York, N.Y. Academic Press, 1975. However, SPD-PAGE revealed a molecualr weight of 36,000, similar to that in prostate tissue and seminal plasma.

Alternatively to the conventional techniques for preparing antibodies in laboratory and farm animals, monoclonal antibodies against PA can be prepared using known hybridoma cell culture techniques. In general, this method involves preparing an antibody-producing fused cell line, e.g. of primary spleen cells fused with a compatible continuous line of myeloma cells, and growing the fused cells either in mass culture or in an animal species from which the myeloma cell line used was derived or is compatible. Such antibodies offer many advantages in comparison to those produced by innoculation into animals, as they are highly specific and sensitive and relatively "pure" immunochemically.

The full potential of this prostatic antigen in clinical applications is not known at present, as it does not appear to exhibit any tumor specificity or pathological association. However, as in the case of acid phosphatase which is present in all prostate tissues, this prostate antigen can provide useful clinical information upon serum monitoring. Recent experiments in our laboratory have shown that the prostate antigen is detected, by rocket immunoelectrophoresis and enzyme-linked immunoassay techniques, in the sera of some prostate cancer patients but not in the sera of normal healthy persons or of patients with other cancers. Further experiments have shown that PA is histologically detectible in both prostate tissue and established continuous tissue culture cell lines of prostate origin, and that it is released by prostate tumor cells, both in vivo and in vitro. In addition, it has been found that the PA level in serum of patients suffering from prostatic cancer is unrelated to the serum levels of prostatic acid phosphatase, so that simultaneous determination of circulating PA and circulating prostatic acid phosphatase may well provide an improved means of diagnosing prostatic cancer. The human prostate antigen, although an eutopic component of the prostate, can thus play a major role in the detection of prostate cancer.

For the preparation of immunogens suitable for preparing diagnostic antibodies against the human prostate antigen, conventional vaccine preparation techniques can be used. Preferably a non-antigenic adjuvant, e.g. alum, Freund's complete adjuvant, saponin, a quaternary ammonium surfactant, an alkyl amine, etc. is admixed with the purified prostate antigen in a suitable immunologically acceptable, non-antigenic carrier and the resultant mixture can be sterilized, e.g. by filtration.

The vaccine can be administered parenterally following regimens already known for immunization with other proteins to stimulate the formation of immunoprecipitating antibodies, with the primary inoculation being preferably followed up by at least one additional injection one to ten weeks later. Good results have been obtained in rabbits using four booster injections at two week intervals one month after the primary immunization. The protein content per injection in rabbits, goats and other mammals can be varied, but is generally about 50 micrograms of protein per kg. of body weight. The antibodies can be collected and worked up using methods well known to those skilled in the art of immunochemistry, and provide a useful reagent for the immunological detection of prostate specific antigen in a variety of immunochemical procedures, e.g., immunoprecipitin, fluorescent antibody, serum neutralization, etc. Such antibodies are useful as a control reagent in the diagnostic test for prostatic cancer described more particularly below.

The simplest immunoprecipitin test involves capillary tube precipitin testing, wherein separate antibody and antigen solutions are allowed to react at a common interface in a capillary tube and a positive reaction is indicated by the formation of a precipitate at the interface. This method is relatively insensitive and inaccurate due, inter alia, to unavoidable diffusion of the two solutions across the interface, and furthermore the final test results cannot be preserved.

Agar gel diffusion is the simplest method which avoids these drawbacks. A solution of the antigen (or serum sample) is placed in a central well punched in a continuous agar gel and appropriate dilutions of the serum containing antibodies (or, correspondingly, the antigen) thereto are placed in wells concentrically surrounding the center well. A positive reaction is noted by the formation of the precipitin line between one or more of the concentric wells and the central well. This method is relatively insensitive and fairly slow, requiring 1 to 4 days to read the test results.

Radioimmunoassay (RIA), e.g. radioimmunoprecipitin tests, are extremely sensitive (by several orders of magnitude over older methods) but take several days to perform and require sophisticated equipment and highly trained personnel not always widely available.

Countercurrent immunoelectrophoresis (CIEP) is a widely used immunoprecipitin method which takes only about an hour to perform and which is considerably more sensitive than agar gel diffusion. Reactive components are placed in opposing wells cut into an agar gel and a small electrical current applied thereto, causing both the antigen and the antibody to migrate towards each other. A positive reaction is indicated by the formation of a precipitate at the antigen-antibody interface. Since this test method is reasonably reliable, readily available and inexpensive, it represents a preferred embodiment of this aspect of the present invention.

For purposes of immunoelectrophoresis testing, the diagnostic antibody preparation of the present invention when used without purification is generally diluted with phosphate buffered saline in a volume ratio of 1:10 to 1:500, depending on the antibody titer thereof. The limiting factor at the lower end of the range is the degree of distinction achieved in the precipitin lines, which is a function of the antibody content in the total protein present. Purified antibody preparations can of course have lower total protein concentrations, and the protein content of even the unpurified preparations can be varied to suit the particular immunochemical test to be employed, the optimal amounts being determined, e.g. by testing simple serial dilutions.

In a preferred, further aspect of the present invention, circulating human prostate antigen can now be detected by immunochemical techniques, preferably by protein staining of the antibody-antigen precipitin complex. Using the aforementioned specific antisera and coupling this with a conventional means for detecting the antigen-antibody complex, it is now possible to immunochemically separate the specific human prostate antigen from a serum sample.

The antigen-antibody complex can be stained by a number of known histochemical staining techniques, e.g. fluorescent antibody, etc., to increase the sensitivity of this method. Alternatively, one can use radioactive antibody for the assay, which not only provides a better quantitative value but may also further increase the sensitivity of the assay. If desired, an enzyme, e.g. β-galactosidase or peroxidase, can be coupled with purified antibodies for use in an enzyme-linked immunoassay, e.g. using techniques analogous to those described by Kato et al. in J. Immunol. 116: 1554 (1976), the contents of which are incorporated by reference herein. Especially preferred is the method described by M. Kuriyama et al. in Cancer Res. 40: 4658 (1980), the contents of which are incorporated by reference herein.

It is preferable to bind these antibodies onto a water-insoluble support for use in the enzyme assay. Many suitable such supports and techniques for binding proteins thereto are well known in the art and include inorganic as well as organic supports. Presently preferred are those water-insoluble supports which can be activated with a cyanogen halide, preferably cyanogen bromide, prior to the covalent bonding of the antibodies thereto, e.g. as taught by Axen et al. in U.S. Pat. No. 3,645,852, the contents of which are incorporated by reference herein. Such supports are commercially available, e.g. the Enzymobeads available from Bio-Rad Laboratories.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

Protein concentration was determined by the method of Lowry et al. described in J. Biol. Chem. 193: 265 (1951), using bovine serum albumin as the standard. Acid phosphatase activity was measured by the method of Babson and Phillips using α-naphthyl phosphate as the substrate.

Immunoprecipitation techniques were modified from B. Weeke, Scand. J. Immunol. (Supplement 1)2: 37–46 (1973). Rocket-IEP was performed on cellulose acetate membranes using 0.83 percent agarose (Sigma low electro-endo-osmosis) in 0.08 M tris-0.024 M tricine-0.024M sodium barbital containing 1.3 mM calcium lactate and 0.02 percent sodium azide (TTB buffer). Antiserum at various final concentrations (0.5–2.0 percent) was incorporated into the agarose at 55° C. prior to plating. Rocket-IEP samples were applied to circular wells (5.0 mm) and electrophoresed at 5 volts/cm overnight at 4° C. using TTB running buffer.

Crossed-immunoelectrofocusing was performed in the second dimension as for rocket-IEP. Isofocused acrylamide gels (5×100 mm) were molded into the antibody-agarose prior to immunoelectrophoresis modified from J. Soderholm et al., Scand. J. Immunol. (Supplement 2) 4: 107–113 (1975). The first dimension isofocusing was done in 7.5 percent polyacrylamide containing 2 percent ampholytes, pH range 4–8 at 200 volts overnight at 4° C. For some experiments, isofocused gels were laid on cellulose acetate membrances and covered with 1 percent agrose. Troughs were cut adjacent to the embedded acrylamide gel, the antiserum placed in the parallel troughs was allowed to diffuse for 24–48 hours at 25° C. and the resulting immunoprecipitin lines were recorded.

Crossed-immunoelectrophoresis (cross-IEP) was performed in the second dimension as for rocket-IEP. The first dimension electrophoresis was performed with 1 percent agarose, and samples (75 μl in rectangular wells) were electrophoresed at 15 volts/cm for 2 hours at 4° C. Migration was monitored with Bromphenol Blue dye.

The abbreviations used are: PB-NaCl, 0.05 M phosphate buffer containing 0.15 M NaCl, pH 7.2; IEP, immunoelectrophoresis; TTB, Tris-Tricine-Barbital (0.08M, 0.042M, 0.024M) buffer containing 0.3 mM calcium lactate and 0.02 percent sodium azide, pH 8.8; $M_R$, relative immunoelectrophoretic mobility; pI, isoelectric point; m.w., molecular weight.

EXAMPLE 1

Extraction of Tissues

Human prostatic tissues (normal, benign hypertrophic, malignant) and other human tissues were obtained during autopsy or surgery. The histology of each issue was confirmed by pathologists. Approximately 10 g of tissues were minced and washed three times with 30 ml of physiological saline, then mixed with 30 ml of 0.02 percent (w/v) disodium ethylenediamine tetraacetate (EDTA)-0.1M phosphate buffered saline (PBS), pH 6.8. The mixture was placed in an ice-water-chilled blending chamber of a Sorvall Omnimixer and subjected to three 5-minute blendings at a blade speed of 25,000 rpm with intermittent cooling time of 3 minutes. The homogenate was stirred overnight at 4° C., then centrifuged at 25,000 g for 30 minutes. The resultant supernatant constituted the crude tissue extract.

EXAMPLE 2

Ammonium Sulfate Fractionation

Pooled prostate tissues, 100 g, were extracted with 300 ml of EDTA-PBS as described above. Ammonium sulfate (60 g) was added to 285 ml of crude extract (35 percent saturation), mixed for 30 minutes and centrifuged (26,000 g, 30 minutes). 38 g of ammonium sulfate were added to 295 ml of the resulting supernatant, (55 percent saturation), mixed for 30 minutes and centrifuged. The precipitate was dispersed in 200 ml of 55 percent saturated ammonium sulfate solution and centrifuged. Washing of the precipitate was repeated twice, then the precipitate was dissolved in 20 ml of 0.01M tris-HCl buffer, pH 8.0. The residual ammonium sulfate was removed by dialysis against 4 liters of the tris-HCl buffer for 48 hours with one change of buffer during dialysis. The dialyzed solution was centrifuged at 46,000 g for 30 minutes to remove any precipitate formed during dialysis.

EXAMPLE 3

Ion Exchange Chromography of Prostate Antigen

The supernatant from Example 2, 28 ml, was applied onto a DEAE-BioGel A column (2.5×93 cm) pre-equilibrated with 0.01M tris-HCl buffer, pH 8.0. The column was first washed with 420 ml of buffer, then eluted with 0–0.2M NaCl gradient (1 liter 0.01M tris-HCl buffer, pH 8.0 in mixer and 1 liter of 0.2M NaCl 0.01M tris-HCl, pH 8.0 in the reservoir) at a flow rate of 6.5 ml/hr/cm$^2$. The effluent was collected (10 ml/fraction) and monitored for the prostate antigen. Gel diffusion according to the method of T. M. Chu et al. in Cancer Treat. Reports 61: 193 (1977) was used to measure the presence of prostate antigen in various chromatographic fractions. The entire procedure was carried out at 4° C. The prostate antigen-containing fractions were pooled and concentrated with an Amicon concentrator fitted with a UM2 ultrafiltration membrane to 4.5 ml.

EXAMPLE 4

Gel Filtration of Prostate Antigen

A portion (4.3 ml) of the concentrated solution was applied onto a Sephadex G-100 column (2.5×110 cm) pre-equilibrated with 0.01M tris-HCl buffer, pH 8.0, which was eluted with same buffer at a flow rate of 3.5 ml/hr/cm$^2$. The pooled DEAE-BioGel A fractions 100–150, containing the prostate antigen upon Sephadex G-100 chromatography, were resolved into several protein peaks. The prostate antigen was found to be in fractions 46–56. Again, the fractions exhibiting prostate antigen reactivity were pooled and concentrated to 3.8 ml.

EXAMPLE 5

Further Purification of Prostate Antigen

The above fractions containing prostate antigen were applied onto a Sephadex G-75 column (2.5×113 cm) pre-equilibrated with tris-HCl buffer; the column was eluted at a flow rate of 5.5 ml/hr/cm$^2$. This resulted in one major symmetrical protein peak associated with the prostate antigen reactivity and two minor protein peaks. When the fractions containing the prostate antigen were re-chromatographed on the same column, an identical symmetrical protein peak was obtained and the minor protein peaks were eliminated. Acid phosphatase activity was measured colorimetrically and histochemically as described by Babson et al. in Clin. Chim. Acta 13: 264–165 (1966) using α-naphthyl phosphate as the substrate. No prostatic acid phosphatase was detected in the chromatographic fractions of this protein peak.

EXAMPLE 6

Analytical Polyacrylamide Electrophoresis

Acrylamide gel (7.5 percent) columns (50×60 mm) were made according to the company's instruction manual (Shandon Southern Instruments, Ltd., Camberley, England), and 50 μl of sample (10–40 μg protein in 25 percent sucrose solution) were applied onto each gel column. Ten percent sucrose solution was then layered carefully above the sample solution, followed by layering 0.05 M tris-glycine buffer, pH 8.5 to the top of the gel-containing tube. Tris-glycine buffer was used in preparing the sucrose solutions and used also as the electrolyte. After electrophoresis with a constant current of 5 mA per tube for 40 minutes, the gels were stained for protein by Coomassie brilliant blue G-250-perchloric acid solution.

EXAMPLE 7

Sodium Dodecyl Sulfate (SDS) Polyacrylamide Gel Electrophoresis

The method was essentially the procedure or Weber and Osborn described in J. Biol. Chem. 244: 4406 (1969). A sample (10–20 μg protein) in 50 μl of 0.05M tris-glycine buffer, pH 8.5, containing 250 μl SDS and 2-mercaptoethanol each, was incubated at 37° C. for 2 hours. After incubation, the sample was mixed with an equal volume of 50 percent sucrose, and 50 μl were subjected to the polyacrylamide gel (containing 0.1 percent SDS) electrophoresis as described before. After electrophoresis, the gels were stained for protein with 0.5 percent (w/v) Coomassie brilliant blue G-250 in ethanol-acetic acid-water (45:10:45, v/v).

EXAMPLE 8

Preparative Polyacrylamide Gel Electrophoresis

Although Sephadex G-75 chromatography produced a symmetrical protein peak with exhibited immunological reactivity of the prostate antigen, the analytical polyacrylamide gel electrophoresis of Examples 6 and 7 revealed several protein components in this preparation. Therefore, a preparative polyacrylamide gel electrophoresis (PAGE) was further used in the purification of prostate antigen.

One ml of specimen (4.5 mg protein) was mixed with 1 ml of 50 percent (w/v) sucrose solution and applied onto an annular 7.5 percent gel column (cross-sectional gel area, 4.4. cm$^2$; height, 9.2 cm), followed by successive layerings of 2 ml of 10 percent sucrose and 0.05M tris-glycine buffer, pH 8.5. A constant current of 30 mA was first applied for 1 hour, and 80 mA thereafter. The tris-glycine buffer was continuously pumped at a flow rate of 14–15 ml/hour into the elution plate located at the bottom of the column to carry materials emerged from the column into a fractional collector. Fractions containing the prostate antigen, representing the final purified preparation, were pooled and concentrated to 0.5 ml. The prostate antigen was found in fractions 28–62 (eluates obtained between 4–9 hours after electrophoresis). When these fractions were pooled and subjected to analytical polyacrylamide gel electrophoresis, multiple protein bands still existed. However, by pooling fractions 56–62 (between 8.1–9.2 hours of electrophoresis) only a single protein band was obtained upon analytical polyacrylamide gel electrophoresis and sodium dodecyl sulfate polyacrylamide gel electrophoresis.

That the final prostate antigen preparation was of high purity was indicated by a single protein band without any contaminating components in polyacrylamide gel electrophoresis in the absence and the presence of sodium dodecyl sulfate. The purified prostate antigen was shown to have a molecular weight of 33,000 by gel filtration on Sephadex G-75, and 34,000 by sodium dodecyl sulfate polyacrylamide gel electrophoresis with no subunit component. Isoelectric focusing revealed a single pI of 6.9.

EXAMPLE 9

Simplified Purification of Antigen from Tissue

The procedure for the purification of PA reported in the preceding Examples takes at least two weeks and yields less than 0.5 mg of purified PA per 100 g of prostatic tissue. Furthermore, for the final step of purification, a painstaking construction of the polyacrylamide gel column as well as a special electrophoretic apparatus are necessary, and problems such as clogging of the elution channel during operation often developed. In this simplified procedure, in addition to the elimination of Sephadex G-75 chromatography and the application of short DEAE columns, the tedious preparative gel electrophoresis has been replaced by a simple pH gradient elution of the DEAE column. The yield of purified PA has increased to 1 to 2 mg per 100 g of prostatic tissue and the entire procedure has been shortened to 8 to 9 days.

Benign hypertrophic prostatic tissues (approximately 100 g) were extracted with disodium tetraacetate-phosphate buffered slaine as described in Example 1 except that the homogenate was stirred for only 2 hours rather than overnight. The crude extract was then subjected to fractional precipitation by ammonium sulfate (30 to 50 percent saturation). The precipitate was dissolved in 10 to 15 ml of 0.01M tris-HCl buffer, pH 7.8, and dialyzed against 4 ml of the same buffer for 48 hours with one change of buffer. The dialyzed materials were centrifuged (46,000 g, 30 min) and the supernatant (12 to 18 ml) was applied onto a 2.5×15 cm DEAE-BioGel A column pre-equilibrated with 0.01M tris-HCl buffer, pH 7.8. The column was washed with ca. 300 ml of the same buffer, followed by elution with 0.08 M NaCl-0.01M tris-HCl buffer, pH 7.8. Fractions containing PA were pooled, concentrated (5 to 5.5 ml), and applied to a 2.5×100 cm Sephadex G-100 column pre-equilibrated with 0.01M tris-HCl buffer, pH 7.8, which was then eluted with the same buffer at a flow rate of 5 ml per hour per $cm^2$. Fractions covering a molecular weight region of 26,000 to 37,000 which contained PA were pooled, concentrated (5 ml) and applied to a 2.5+20 cm DEAE column pre-equilibrated with 0.01M tris-HCl buffer, pH 7.8. The column was washed with 10 ml of the same buffer, followed by elution with pH gradient solution (mixer: 0.01M tris-HCl, pH 7.0, 300 ml; reservoir: 0.01M tris-HCl, pH 6.0, 500 ml) at a flow rate of 5 ml per hour per $cm^2$. Second peak fractions which contained PA were pooled and concentrated.

Table 1 summarizes the results of a typical purification of PA from prostatic tissue by this simplified procedure. Although modification at the salt precipitation step led to lesser recovery of PA, a large quantity of contaminating proteins such as hemoglobin were removed, thereby facilitating further purification of PA. Radial immunodiffusion used in this study was the technique of Mancini et al described in Immunochem. 2: 235–254 (1965), with modifications. Anti-PA serum (100 μl) was mixed with 10 ml of 1 percent agarose solution (in 0.154M NaCl-0.017M solium phosphate, pH 7.0) at 55° C. and poured into a Petri dish (diameter: 8.3 cm). Wells (diameter: 2 mm) were then made on the agarose gel and to each well, 10 μl of sample was added. For monitoring PA in the chromatographic fractions, overnight diffusion was sufficient to reveal precipitin; for quantitation of PA, the diffusion was allowed to continue for 48 hours, followed by washing of the gel for 2 days with 0.154M saline and subsequent staining with Coomassie Brilliant Blue G-250.

TABLE 1

Purification of Prostate Antigen from Human Prostatic Tissue

| Steps | Total volume (ml) | Total protein (mg) | Total PA (mg) | Folds purification | Recovery (percent) |
|---|---|---|---|---|---|
| Crude extract[a] | 258.0 | 1754.4 | 20.6 | 1 | 100 |
| Ammonium sulfate (30–50 percent) | 13.8 | 278.8 | 10.0 | 3.1 | 48.5 |
| First DEAE | 5.5 | 80.9 | 7.9 | 8.3 | 38.3 |
| Sephadex G-100 | 5.0 | 9.3 | 4.3 | 39.4 | 20.9 |
| Second DEAE | 5.0 | 1.5 | 1.5 | 85.2 | 7.3 |

[a]From 118 g of benign hypertrophic prostate tissues.

EXAMPLE 10

Purification of Antigen from Fluid

PA was also purified from 20 ml of seminal plasma according to the procedure of Example 9 except that the extraction step was omitted and that, in the second step, PA was precipitated by ammonium sulfate at a concentration of 30 to 75 percent saturation. The results are shown in Table 2.

TABLE 2

Purification of Prostate Antigen from Human Seminal Plasma

| Steps | Total volume (ml) | Total protein (mg) | Total PA (mg) | Folds purification | Recovery (percent) |
|---|---|---|---|---|---|
| Seminal plasma | 16.2 | 595.2 | 8.8 | 1 | 100 |
| Ammonium sulfate (30–75 percent) | 20.0 | 266.2 | 7.4 | 1.9 | 84.1 |
| First DEAE | 5.3 | 61.0 | 5.7 | 6.3 | 64.8 |
| Sephadex G-100 | 6.4 | 12.8 | 4.5 | 23.8 | 51.1 |
| Second DEAE | 4.5 | 1.5 | 1.5 | 67.6 | 17.0 |

EXAMPLE 11

Molecular Weight Determination

In order to obtain an approximate molecular weight of the prostate antigen present in crude prostate tissue extracts and in antigen-positive patients' sera, these samples were subjected to a Sephadex G-200 gel filtration chromatography. Serum samples (0.5 ml) previously shown to be prostate antigen-positive by rocket-IEP, or prostate tissue extracts (0.5 ml containing 8 mg protein) were applied to a column (0.9×60 cm) packed with Sephadex G-200 gel in PB-NaCl. Eluted samples were analyzed for absorbance at 280 nm and prostate antigen level was determined by rocket-IEP using a sample size: 0.5 ml; equilibration buffer: PB-NaCl (pH 7.2); fraction size; 0.8 ml; elution rate: 10 ml per hour. Peak antigen activity as exhibited in prostate tissue extracts eluted between 30–40,000 m.w. Molecular weight reference markers included human immunoglobin G (160,000), bovine serum albumin (68,000), ovalbumin (43,000), chymotrpysinogen A (25,000) and ribonuclease A (13,700). In antigen-positive patient sera examined by gel filtration, prostate antigen eluted as a single symmetrical peak between 80–100,000 m.w.

EXAMPLE 12

Preparation of Antisera

Female rabbits were immunized as described previously by T. M. Chu et al. in Investigative Urology 15: 319–323 (1978) with the crude extract of normal human prostatic tissue (for antiserum $P_8$), or with a purified prostate antigen (for antiserum $P_{17}$) obtained at the Sephadex G-75 step described above. Sera were collected, heat inactivated and stored at −20° C. until use. Absorption of the antiserum with normal female serum (NFS) or tissue extracts (10 mg protein/ml) was carried out as described by T. M. Chu et al. in Cancer Treatment Reports 61: 193–200 (1977).

EXAMPLE 13

Specificity of Antiserum Raised Against Crude Prostate Antigen

Immunoelectrophoresis was performed on a 9.5×10.2 cm agarose (0.65 percent, w/v) plate. Barbital buffer, (pH 8.2, ionic strength 0.04) was used as the electrolyte and a constant voltage of 90 V. was applied for one hour. After electrophoresis and gel diffusion (20 hours), the plate was washed with 0.154 M saline for 2 days and stained first for acid phosphatase with a solution of α-naphthyl phosphate-fast garnet GBC salt in 0.1M ammonium acetate, pH 5.0, and then for protein with Coomassie brilliant blue G-250-perchloric acid solution.

Immunoelectrophoresis of the crude extract prepared from normal prostatic tissues and antiserum $P_8$, an antiserum raised against the crude extract of normal prostate, resulted in three precipitin arcs. One of these arcs was formed by a normal human serum component, as it disappeared after the antiserum was absorbed with normal female serum (NFS-$P_8$). Absorption of the antiserum NFS-$P_8$ with various normal human tissue extracts (urethra, bladder, heart, lung, pancrease, bone, kidney, intestine, liver and spleen, 10–20 mg each per ml) failed to eliminate the two remaining precipitin arcs, one of which was identified as prostatic acid phosphatase since it was stained with the α-naphthyl phosphate-fast garnet GBC salt solution. The other precipitin arc was shown to be a prostate tissue-specific antigen, identified as a protein, not stainable for acid phosphatase activity, which migrated with β-mobility upon IEP analysis. Absorption with an extract of normal human prostate removed the reactive antibodies from the antiserum NFS-$P_8$ and abolished both precipitin arcs. Furthermore, this antigen was demonstrated in all 20 of 20 normal prostates and identical results were obtained with the extracts of benign hypertropic (15/15) and cancerous prostatic (8/8) tissues. These data demonstrate that normal, benign hypertrophic and malignant prostate contain a prostatic tissue-specific antigen in addition to prostatic acid phosphatase.

EXAMPLE 14

Specificity of Antiserum Raised Against Purified Prostate Antigen

Following the procedure of Example 11, additional confirmation was provided with the use of antiserum $P_{17}$ raised against a purified preparation of the prostate antigen, which was devoid of prostatic acid phosphatase. Both gel diffusion and immunoelectrophoresis employing the normal adult male and female serum-absorbed antiserum $P_{17}$ resulted in a single immunoprecipitation of the prostate antigen. The extracts prepared from tissues other than the prostate did not react with the normal female serum-absorbed antiserum $P_{17}$.

EXAMPLE 15

Immunological Identity of Tissue and Serum Prostate Antigen

In order to determine if the serum-borne antigen shared immunological or biochemical characteristics with the antigen detected in prostate tissue extracts, the following experiments were performed. Samples of sera and prostate tissue extracts were subjected to rocket-IEP both individually and immediately after combination of both antigen sources. In each experiment, the samples were adjusted to the same final protein concentration by the use of buffer dilutions. A representative experiment employed two sample wells containing patient sera, sample wells containing prostate tissue extract and two sample wells containing a mixture of patient's serum and tissue extract to demonstrate peak enhancement. Sera and tissue extracts were at the same final protein concentration in each well by the use of appropriate volumes of diluting buffer (PB-NaCl). All samples were 25 μl; one percent antibody in 0.83 percent agarose; 5 V per cm, 20 hours at 4° C. All samples produced a single immuno- precipitate when assayed individually. Mixing samples, in peak enhancement experiments, produced a single reaction whose height was greater than that of individual samples. When antigen-positive serum samples and prostate tissue extracts were mixed and immediately subjected to crossed-IEP, a fused immunoprecipitation peak resulted. Both methods of quantitative immunoelectrophoresis, showing peak enhancement and immunoprecipitate fusion, confirmed the immunological identity of the prostate antigen as it occurs in tissue and serum according to the method of N. H. Axelson et al. in Scand. J. Immunol. (Supplement 1) 2: 91–94 (1973).

It should be noted that results regarding prostate antigen, as detected in tissue, apply to extracts prepared from normal, benign hypertropic and malignant prostate specimens; no physical differences in prostate antigen (i.e., $M_R$, pI or m.w.) were observed among these antigen sources, and extracts prepared from benign and malignant prostate specimens exhibited immunoprecipitation lines of identity with normal prostate when tested against anti-prostate antigen antiserum by double immunodiffusion. In addition, the relative level of prostate antigen was compared among extracts prepared from normal, benign hypertrophic and malignant prostate tissues. As determined by rocket-IEP (Table 3) no statistically significant difference of antigen level was observed between these antigen sources and a wide variation in antigen level (indicated by the large standard deviations calculated) was also noted to occur for each category of tissue extract examined.

TABLE 3

PROSTATE ANTIGEN LEVELS IN PROSTATE TISSUE EXTRACTS[a]

| Tissue Pathology[b] (Number) | Prostate Antigen Level ± S.D. |
|---|---|
| Normal (4) | 14.3 units[c](± 8.7) |
| Benign hypertrophic (8) | 18.4 units[c](± 21.3) |
| Primary carcinoma (8) | 13.0 units[c](± 13.8)[d] |

[a]Each tissue extract was adjusted to 1 mg protein per ml prior to analysis for prostate antigen by rocket immunoelectrophoresis.
[b]All tissue specimens were bistopathologically confirmed.
[c]For this experiment, one unit was arbitrarily chosen to represent one percent of the antigen level of a reference prostate extract. The reference extract was assayed in a dilution series and run on the same plates as experimental extracts.
[d]As analyzed using Student's t-test, no statistically significant difference was found among these groups.

EXAMPLE 17

Immunological Identity of Fluid and Serum Prostate Antigen

Since prostatic acid phosphatase has been reported in both prostatic tissue and seminal fluid, we wished to determine whether PA also exists in the seminal fluid. Anti-PA serum, raised against PA isolated from prostatic tissue, reacted in immunodiffusion with crude extract of prostatic tissue, as well as with seminal plasma, and formed a fused line, indicating immunologic identify of the PA in prostatic tissue with that in seminal plasma. By the previously described radial immunodiffusion procedure, the PA concentration in seminal plasma was found to be 0.4 to 1.8 mg/ml, while 1 g. of prostatic tissue contained 0.15 to 0.45 mg of PA extractable with disodium ethylenediamine tetraacetate-phosphate buffered saline (EDTA-PBS).

EXAMPLE 18

Histological Localization of Prostate Antigen

Localization of PA in the prostate gland as well as specificity of PA have been probed with the immunoperoxidase staining technique of Heyderman and Neville reported in J. Clin. Path. 30: 138–143 (1977). Sections of freshly fixed prostatic tissue were deparrafinized in two changes of xylol, rehydrated thru a graded series of ethanol, and washed with distilled water. Following the inhibition of endogeneous peroxidase activity by 7.5 percent $H_2O_2$, the reactivity of anti-PA was assessed with rabbit anti-PA serum. After incubation and subsequent washing, the tissue sections were further incubated with peroxidase-labelled goat anti-rabbit $\gamma$-globulin. Excessive enzyme-labelled second antibody was then removed by washing, and the tissue sections were stained for peroxidase activity. As controls, the substrate alone, substrate plus conjugate, pre-immune rabbit serum, and anti-PA preabsorbed with specific antigen were used.

It was observed that the staining was restricted to epithelial cells comprising the prostatic ductal elements. An intense staining was shown in the apical cytoplasma of these cells, but no staining was seen in the nuclei. Within several ductal elements, positively staining secretory material was observed in the section examined. Specific staining was not observed for other cellular elements, including stromal and vascular elements. Using the same technique, PA could not be detected in sections derived from other organ tissues, including the pancrease, colon, stomach, liver, seminal vesicles, and testes. Employing similar immunohistochemical techniques, PA has been demonstrated in all primary and metastatic prostatic tumors tested, but not in non-prostatic cancer tissues.

EXAMPLE 19

Detection of Prostate Antigen in Established Tissue Culture Cell Lines

To determine if malignant cells in long-term culture retain the expression of PA, three established strains of prostate cells (LNCaP, PC-3, and Du-145) were examined. Extracts prepared from these cells and other cultured cells of nonprostate origins were assayed for the presence of PA by the previously mentioned Enzyme Immunoassay (EIA) procedure capable of detecting 1 ng PA/ml.

Immobilized anti-PA was prepared using CNBr-activated Sepharose 1B (Pharmacia Fine Chemicals). The reaction mixture consisted of 5 g of CNBr-activated Sepharose and 130 mg of IgG (anti-PA) in 0.1M borate buffer (pH 8.5) containing 0.5M NaCl. After incubation at 4° C. for 18 hours, the beads were washed with borate buffer and post-treated with a 1-M ethanolamine solution (pH 9.0) to block unreacted groups. Covalently coupled beads were further washed and stored in PBS at 4° C.

For the EIA, 100 $\mu$l of an antigen sample was mixed with 300 $\mu$l of a fifty fold-diluted immobilized antibody and incubated for 3 hours at room temperature. After the addition of 1 ml assay buffer (PBS containing 1 percent BSA), the mixture was centrifuged at 1,000 g to wash the beads. This procedure was repeated twice. To the washed beads was applied 100 $\mu$l of peroxidase-IgG (anti-PA) conjugate in assay buffer. After a further incubation for 18 hours at room temperature, the beads were again washed as described above and assayed for the amount of bound peroxidase activity present. The reaction mixture contained 0.08 percent dianisidine and 0.003 percent $H_2O_2$ in 0.01 M sodium phosphate buffer (pH 6.0) and was allowed to react with the beads for 90 minutes. The enzyme reaction was then stopped with 100 $\mu$l of 1 N HCl, and the absorbance at 403 mn was determined. Each run included standards of known prostate antigen concentration. Using this assay procedure, linearity of of the dose-response curve was achieved between 1 and 20 ng PA/ml. Before reexamination, samples containing higher levels of antigen were serially diluted with assay buffer. The results indicated that two lines of prostate cancer cells, LNCaP and PC-3, contained significant levels of PA (50–700 ng/ml) as compared with those found in Du-145 and other cell lines examined (less than 4 ng/ml). PA was also present in conditioned "spent" media derived from prostate cultures producing the antigen.

EXAMPLE 20

Immunological Reactivity of Cultured Prostate Cells with Immunoglobulin Antiserum Fragments To further assess antibody specificity, we examined cultured cells for their ability to specifically accrete radiolabeled antibody fragments. Included in these experiments were cells derived from the prostate gland (LNCaP), colon (HT-29), and breast (MCF-7). For the preparation of immunoglobulin fragments, samples of IgG, anti-PA and rabbit pre-immune serum were dissolved in 0.1M sodium actate buffer (pH 4.0). For every 50 mg of IgG, 1 mg of crystallized pepsin was added and the reaction mixture was incubated overnight at 37° C. $F(ab')_2$ fragments were separated from unreacted IgG and from smaller peptides by gel filtration over Sephacryl S-300 (Pharmacia Fine Chemicals) equilibrated in PBS buffer. The column (2.6×70 cm) was calibrated by the chromatography of molecular weight standards, including IgG, BSA, and egg albumin. Isolated $F(ab')_2$ fragments were concentrated by ultrafiltration with the use of an Amicon PM-10 membrane and positive pressure.

Trace labeling of $F(ab')_2$ fragments was accomplished with the use of solid-phase lactoperoxidase-glucose oxidase (Enzymobeads; Bio-Rad Laboratories). To 1 mg of $F(ab')_2$ were added 50 $\mu$l of Enzymobeads, 25 $\mu$l of 1 percent $\beta$-D-glucose, 200 ml of 0.2 M sodium phosphate (pH 7.0), and 1 mCi of carrier-free $^{131}I$ or $^{125}I$.

The reaction was allowed to proceed for 30 minutes at room temperature. Unreacted iodide was separated from labeled protein by gel filtration over Sephadex G-25. Specific activities of trace-labeled $F(ab')_2$ preparations ranged between 0.6 and 0.8 $\mu Ci/\mu g$.

Cells grown in 24-well culture dishes with each well containing $1.5\times10^6$ cells were incubated with a paired radiolabeled mixture of $^{125}I$-labeled $F(ab')_2$ (anti-PA) and $^{131}I$-labeled $F(ab')_2$ (preimmune) in fresh media. This mixture contained $1.5\times10^5$ cpm for each radioactive nuclide and was allowed to react with cultured adherent cells overnight under standard conditions. To determine radioactive uptake, cells were scraped from the wells and washed three times in PBS before counting for each radioactive nuclide in a Packard automatic $\gamma$-scintillation counter. Preferential uptake of a specific radioactive nuclide was calculated as a localization ratio: ($^{125}I$ cell bound $^{131}I$ cell bound): ($^{125}I$ added $^{131}I$ added). A specific localization ratio was calculated for each cell type, and the results indicated a significantly higher antibody uptake by the LNCaP cells of prostate origin than for the HT-20 or MCF-7 cells.

EXAMPLE 21

Release of Prostate Antigen by in vivo Tumor Cells

When established as tumor cell xenografts in nude mice, LNCaP cells released detectable levels of PA into the circulation of these animals. Congenitally athymic nude mice homozygous for the nu/nu allele were bred at Roswell Park Memorial Institute from matings of BABL/c nu/nu homozygous males and BALB/c+/nu heterozygous females. Human tumors were established subcutaneously in the nude mice before sera were obtained for PA analysis by the injection of cultured cell suspensions. For this, the cells were washed in PBS, counted for viability, and adjusted to the desired concentration in sterile 0.9 percent NaCl solutions. Subsequent to nodule formation, nude mouse serum was collected by severing the retro-orbital plexus and stored at −20° C. Cell cultures used for the establishment of human tumor grafts included LNCaP (adenocarcinoma of the prostate gland), RT-4 (transitional cell carcinoma of bladder), Palarmo (malignant melanoma), and AsPC-1 (pancreatic carcinoma).

Of the human tumors examined, only the LNCaP prostate line released PA into the circulation, which correlates with results obtained from the assay of cultured cells. The control mice given preimplants of RT-4 cells. Palarmo cells, or AsPC-1 cells showed no detectable PA in their circulation. It is not presently appreciated if serum antigen levels are commensurate with the tumor load, a phenomenon previously reported by E. J. Pesce et al. in Cancer Res. 37: 1998–2003 (1977) for the lactate dehydrogenasde enzyme released by human xenografts. If this is so, then the human prostate tumor-nude mouse system, coupled with detection of PA, can provide a valuable clinical model to monitor the effects of antitumor modalities and the effects of biologic response modifiers for human prostate cancer.

EXAMPLE 22

Antiserum Specificity

The optimal concentration of adsorbed antiserum required in the rocket-IEP procedure was determined by examining the migration of prostate antigen in gels containing varying concentrations of anti-prostate antigen antiserum. The reactivity of various tissues was examined by rocket-IEP. As shown in Table 4, all extracts prepared from normal prostate, benign hypertrophic and malignant prostate tissues showed reactivity, producing a single immunoprecipitin reaction. Extracts prepared from the non-prostate tissues, whether normal or neoplastic in nature, gave no immunologic reactivity.

TABLE 4

REACTIVITY OF ANTI-PROSTATE ANTIGEN ANTISERUM WITH HUMAN TISSUE EXTRACTS[a]

| Tissue | Pathology | Percent Positive Reaction: Rocket-IEP | Percent Positive Reaction: Immuno-difussion |
|---|---|---|---|
| Liver | Normal | 0 (0/2) | 0 (0/1) |
| Spleen | Normal | 0 (0/1) | 0 (0/1) |
| Lung | Normal | 0 (0/1) | 0 (0/1) |
| | Adenocarcinoma | 0 (0/1) | 0 (0/1) |
| Bone Marrow | Normal | | 0 (0/1) |
| Bladder | Normal | 0 (0/1) | 0 (0/1) |
| Breast | Normal | 0 (0/1) | |
| | Adenocarcinoma | 0 (0/5) | |
| Intestine | Normal | 0 (0/1) | 0 (0/1) |
| | Adenocarcinoma | 0 (0/1) | 0 (0/1) |
| Heart | Normal | 0 (0/1) | 0 (0/1) |
| Pancreas | Adenocarcinoma | 0 (0/2) | 0 (0/1) |
| Kidney | Normal | 0 (0/1) | 0 (0/1) |
| Cerebral Cortex | Normal | 0 (0/1) | 0 (0/1) |
| Prostate | Normal | 100 (4/4) | 100 (20/20) |
| | Benign Hypertrophic | 100 (8/8) | 100 (15/15) |
| | Adenocarcinoma | 100 (8/8) | 100 (8/8) |

[a]All tissue extracts were adjusted to 10 mg protein/ml prior to analysis

EXAMPLE 23

Diagnostic Specificity

To examine the potential diagnostic value of the prostate antigen, serum samples were examined for its presence by the method of rocket-IEP, using anti-prostate antigen antiserum treated with normal human plasma to remove antibodies against normal plasma proteins (Table 5). Serum samples obtained from 20 normal healthy adults and 20 male volunteers over the age of 55 years showed no reactivity against the antiserum with this assay. Also, serum was drawn from a total of 175 patients with various advanced malignancies, including patients with malignancies of lung, colon, rectum, stomach, pancreas, thyroid, breast and with myeloma. All sera obtained from patients with non-prostatic malignancies were prostate antigen-negative when assayed by the rocket-IEP procedure. However, out of a total of 219 sera examined from advanced prostatic cancer patients, 17 or approximately 8 percent showed the presence of prostate antigen in circulation. All sera showing a positive reaction for prostate antigen were subsequently subjected to the same assay, and reproducibility of the test was 100 percent.

TABLE 5

REACTIVITY OF ANTI-PROSTATE ANTIGEN ANTISERUM WITH HUMAN SERA BY ROCKET-IEP[a]

| Serum Donors | Percent Positive Reaction |
|---|---|
| Normal adults (male and female) | 0 (0/20) |
| Age-and sex-matched controls | 0 (0/20) |
| Patients with advanced malignancies[b] | |
| Lung carcinoma | 0 (0/83) |
| Thyroid carcinoma | 0 (0/1) |
| Colon-rectal carcinoma | 0 (0/22) |
| Stomach-pancreas carcinoma | 0 (0/34) |
| Breast carcinoma | 0 (0/33) |
| Myeloma | 0 (0/2) |

TABLE 5-continued

| REACTIVITY OF ANTI-PROSTATE ANTIGEN ANTISERUM WITH HUMAN SERA BY ROCKET-IEP[a] | |
|---|---|
| Serum Donors | Percent Positive Reaction |
| Prostate carcinoma | 8 (17/219) |

[a]All sera were abquoted and stored at −20° C. or −70° C. until required. A sample volume of 25 μl was used for all studies.
[b]Each case was pathologically confirmed.

EXAMPLE 24

Enzyme-Linked Immunoassay Tests

Using IgG antibodies against the purified prostate-specific antigen with horseradish peroxidase and CNBr-activated Sepharose 4B as reagents, a sensitive sandwich-type (Sepharose 4B-anti-prostate antigen IgG: prostate antigen: anti-prostate antigen IgG-peroxidase) enzyme-linked immunoassay capable of detecting 0.1 ng of prostate antigen/ml. was evaluated. Of the various normal and tumor tissues examined, only human prostate tissue was shown to contain the prostate antigen (normal prostate 10±21.9 μg prostate antigen/mg. protein, n=6, benign hypertrophy 18.3±29.5, n=12; malignant prostate 19.1±15.3, n=13). Circulating levels of prostate antigen were also quantitated by the same assay; no prostate antigen was detectable in sera from normal females (n=17) or female cancer patients (n=25). Additional results (in ng/ml) are shown in Table 6.

TABLE 6

| ENZYME-LINKED IMMUNOASSAY RESULTS | | | | | |
|---|---|---|---|---|---|
| Group | Mean | S.D. Range | n | α 2.30 | p |
| Normal males | 0.47 | 0.66 0.1-2.6 | 51 | 2 | |
| Non-prostate cancer males | 0.52 | 0.62 0.1-3.0 | 92 | 3 | N.S. |
| Prostate cancer | | | | | |
| Stage A | 8.00 | 5.64 2.8-14 | 3 | 3 | 0.02 |
| Stage B | 7.15 | 3.05 4.6-11 | 4 | 4 | 0.001 |
| Stage C | 10.52 | 17.06 0.3-100 | 44 | 31 | 0.001 |
| Stage D | 22.84 | 30.97 0.2-270 | 250 | 193 | 0.001 |

(p vs. normal males by Student's test; N.S. = not significant)

The prostate antigen from the serum of prostate cancer patients was purified and shown to be immunochemically identical to the prostate antigen for normal prostate tissue. This data, therefore, demonstrate that the prostate antigen described herein, although a histotype-specific antigen of the normal prostate, can be used in the immunological detection of prostatic cancer.

EXAMPLE 25

Prognostic Value of Enzyme-Linked Immunoassay Tests

Using the sensitive enzyme immunoassay reported in Cancer Res. 40: 4658(1980), the circulating PA in prostatic cancer patients has been evaluated clinically. In 96 patients in advanced stage of disease ($D_2$) and receiving chemotherapies, the pretreatment serum PA levels were found to be of prognostic value in regard to patients' survival. Patients who survived more than 12 months (n=10) had serum PA levels of 11.2 ng/ml±12.7 (means±S.D.), and those (n=59) who expired within 5 months exhibited serum PA values of 28.5±31.9; while levels of 13.7±18.2 were found in the patients (n=27) who survived 6-11 months. Nineteen of these patients were monitored by 220 serial PA assays for more than 6 months, and a clinicopathological correlation between PA levels and clinical course was found in 14 patients (74 percent). Additionally, in another group of 32 patients who underwent curative therapies for localized prostate cancer, 161 serum samples were analyzed during a period of 12 to 114 weeks (average 56 weeks). Of these patients, 5 developed metastasis during follow-up and all were shown to exhibit increasingly elevated serum PA values 0-68 weeks preceding the clinical diagnosis of disease recurrence. These results demonstrate that PA is a useful new marker for monitoring prostate cancer.

EXAMPLE 26

Establishment of a Hybridoma Cell Line

A nonsecreting myeloma cell line of Balb/c origin described in J. Immunol. 123: 1548-1550 (1979) was used. This line, P3X63Ag8.653, is derived from the γ-1 K-type producing P3X63Ag8. P3X63Ag8.653 cells were maintained in Dulbecco's modified Eagle's medium (DMEM) containing 15 percent heat-inactivated fetal bovine serum (FBS), 2 mM glutamine, 100 U/ml penicillin, and 100 U/ml streptomycin in a 10 percent $CO_2$/air humidified incubator at 37° C.

Female Balb/c mice (8-10 weeks old) were intraperitoneally injected on days 1 and 30 with 10 μg Prostate Antigen (PA) purified as described in Investigative Urology 17:159-163 (1979). Three to six weeks later, the mice received an intravenous injection of 10 μg PA in sterile saline. All mice used for fusion experiments showed the presence of serum antibodies against PA, as detected using double immunodiffusion against purified PA.

Spleens were aseptically removed from immune mice after the last immunization, placed in 10 ml DMEM-15 percent FBS, and cell suspensions made by teasing with curved forceps. Clumps and membrane fragments were allowed to settle and the resulting single cells were washed once by centrifugation at 600 g for 10 min. Red cells were lysed by incubation in 0.84 percent $NH_4Cl$, and the cells were washed and resuspended in DMEM at a concentration of $2\times10^7$ cells/ml. The myeloma cells were similarly washed and adjusted to $2\times10^7$ cells/ml of DMEM. Three ml of spleen cells were added to 3 ml of myeloma cells and co-pelleted at 600 g for 10 min., and the medium was completely removed. For fusion, the cells were gently resuspended in 1 ml of 30 percent (w/v) polyethylene glycol (PEG), average molecular weight 1,000, in DMEM at pH 8.0. The tube was rocked for 1 min. and centrifuged for 6 min. at 600 g. After a total exposure time to the PEG of 8 minutes, the supernatant was removed and 10 ml DMEM slowly added with continuous circular agitation of the tube. Cells were then centrifuged for 10 min. at 600 g, and gently resuspended in 50 ml of HAT selection medium (DMEM-15 percent FBS containing $1.6\times10^{-5}$M thymidine, $1\times10^{-4}$M hypoxanthine, and $1\times10^{-7}$M aminopterin). One ml amounts were dispensed into 48 wells of multiwell dishes and plates were incubated at 37° C. in a humidified atmosphere of 10 percent $CO_2$ in air. HAT medium was replenished every 4 days until day 21 when hypoxanthine/thymidine (HT) medium was added. As wells turned acid (usually 8-12 days after fusion), supernatants were tested for antibody activity. Samples of hybrid cells from wells which showed positive antibody activity were cloned by limiting dilution and some cells from the same well were transferred to 25 $cm^2$ tissue culture flasks until $2\times10^7$ cells were obtained, which were frozen in liquid nitrogen in 10 percent dimethylsulfoxide-90 percent FBS.

EXAMPLE 27

Selection of Hybridoma Cells

Fusion Supernatants were screened for anti-PA antibodies by a solid-phase enzyme immunoassay. Disposable 96-well microtiter plates were used as the solid absorbing surface. The wells were filled with 100 ml poly-L-lysine succinate (0.25 mg/ml $H_2O$) and incubated at 23° C. for 15 min. Following 3 washes with PB-NaCl pH 7.2 (50 mM sodium phosphate:140 mM sodium chloride), 100 ml of purified PA were added at a concentration of 50 μg/ml 10 mM carbonate buffer, pH 9.6. After incubation for 24 hr. at 37° C., 100 ml of 1 percent (w/v) bovine serum albumin solution in PB-NaCl buffer were added for a further 3 hrs. at 37° C.

Prior to performing the antibody screening assay, the microtiter wells were washed 3 times using PB-NaCl buffer (200 μl). Culture fluids (100 μl) to be tested were applied to individual wells and allowed to incubate at 37° C. for 3 hrs., followed by 3 washes with PB-NaCl buffer. Subsequently, 100 μl of peroxidase-conjugated antiserum to mouse Ig prepared according to the procedure described in J. Immunol. Methods 15: 305–310 (1977) were added to each well and incubated at 37° C. for 3 hours. After 3 washes with PB-NaCl buffer, enzyme activity was revealed using substrate solution containing 0.08 percent o-dianisidine: 0.003 percent $H_2O_2$:0.01 M sodium phosphate, pH 6.0. The enzyme reaction was stopped after 60 min. at 23° C. using 25 μl of 1 N HCl.

In each assay, positive control samples were included and consisted of serially diluted hyperimmune mouse serum raised against purified PA. Tissue culture supernatants from P3X63Ag8 cultures (γ 1-Kappa) and from the parental nonsecreting myeloma line were used as negative controls. This screening assay detects immunoglobulins of the IgG, IgM and IgA classes.

EXAMPLE 28

Cloning of Hybridoma Cells

Desired myeloma hybrids were cloned by limiting dilution in the presence of peritoneal macrophages to increase cloning efficiency. Hybrid cells were plated in 96-well culture dishes at a density of 0.5 cells/well in DMEM-15 percent FBS complete medium. Vigorous growth was observed after 8–12 days, at which time supernatants were tested from wells showing single colonies. Cultures exhibiting antibody activity were re-cloned by this procedure to ensure population homogeneity.

Peritoneal macrophages were prepared by flushing the peritoneal cavity of Balb/c mice with 5 ml of ice cold, sterile 0.34 M sucrose. To attain high yields of macrophages ($5–15\times10^6$/mouse), animals received an intraperitoneal injection of 0.5 ml sterile thioglycolate medium 4 days prior to harvesting the cells. Macrophages were washed once by centrifugation at 600 g for 5 min. and were resuspended at $10^6$/ml in tissue culture medium. Each tissue culture well received 100 μl of macrophage suspension. The hybridoma described herein has been deposited with the American Type Culture Collection, Rockville, Md. 20850, U.S.A. and is designated ATCC No. HB 8051.

EXAMPLE 29

Purification of Monoclonal Antibodies

Monoclonal antibodies from spent culture fluids were purified using immuno-affinity chromatography with rabbit-antimouse Ig: Sepharose 4 B gel matrix (RaMIg-Sepharose). Twenty ml of R-αMIg:Sepharose were packed into a chromatographic column (1.5×30 cm) and equilibrated with PB-NaCl buffer. Samples of culture fluids were slowly passed through the column (5 ml/hr), followed by removal of non-specific reactants by elution with 100 ml of 0.1 M glycine: 1 M NaCl, pH 9.0. Reactive proteins were then eluted with 3 bed volumes of 4 M KSCN:0.01 M sodium phosphate, pH 7.2. Dialyzed materials were concentrated using positive-pressure ultrafiltration.

EXAMPLE 30

Immunodiffusion Analysis of Secreted Hybridoma Products

An affinity matrix was prepared by coupling 200 mg Ig (R-αMIg) to 5 grams of cyanogen bromide-activated Sepharose 4B; an IgG fraction of rabbit antisera to mouse IgG (H+L) was prepared by a Rivanol procedure described in J. Immunol. Methods 15: 305–310 (1977). Coupling was performed at pH 8.0 in bicarbonate buffer according to directions provided by the manufacturer (Pharmacia; Piscataway, N.J.). The class and subclass of isolated anti-PA antibodies were determined by double immunodiffusion in 0.6 percent agarose using rabbit anti-mouse IgG1, IgG2a, Ig2b, IgG3, IgM, anti-K and anti-λ chain.

Supernatants from 96 of the most vigorously growing cultures were screened in duplicate for antibody activity against PA, using a solid phase enzyme-immunoassay. Results indicated that approximately 4 percent (4/96) of cultures were initially antibody-positive. Upon re-assay of these cultures, one hybridoma (F5-A-1/22) remained positive. This culture was cloned by limiting dilution over peritoneal macrophages and yielded 30 cultures which macroscopically exhibited single colonies of growth. One positive culture was re-cloned and all cultures derived therefrom were antibody-positive. These cells (clone F5-A-1/22.8.13, termed Cl. 8.13) were expanded to mass culture and examined for antibody content (Table 7). As a positive control for this experiment, culture fluids from P3X63Ag8 cells, known to produce IgG1 kappa-type immunoglobulen, were used. Cells of the P3X63Ag8 strain produced approximately 12 μg/ml of isolated immunoglobulin which was reactive against specific antisera to IGG1 and K-chain (Table 8). No precipitation occurred with other immunoglobulen subclass antiserum reagents. Culture fluids from Cl. 8.13 showing anti-PA activity contained about 10 μg/ml of isolated material using R-αMIg: Sepharose purification. This isolate was identified as mouse immunoglobulin of the IgM K-type subclass (Table 8). This preparation did not precipitate against other subclass of antisera, indicating monoclonality of the isolated immunoglobulin preparation.

TABLE 7

| Affinity purification of monoclonal antibodies using R-αMIg: Sepharose 4B chromatography[a] | | | |
|---|---|---|---|
| Culture | Culture Fluid (ml) applied to affinity adsorbent | Yield Ig(mg)[b] | μgIg/ml culture fluid |
| P3X63Ag8 | 125 | 1.6 | 13 |
| F5-A-1/22.8.13 | 300 | 3.1 | 10 |

[a]Clarified culture fluids were passed through R-αMIg: Sepharose 4B adsorbent as described. The gel was washed with 1M NaCl pH 9.0 until absorbance at 280 nm reached baseline (less than 0.0200 D units).
[b]R-αMIg-reactive substances were eluted under chaotropic dissociating conditions of 4M KSCN. Yield of Ig isolated was determined by optical density measurements where a 1 percent (w/v) solution of mouse IgG shows an extinction coefficient of 14.

TABLE 8

| Immunodiffusion analysis of affinity purified immonoglobulins from spent culture fluids. Affinity isolates from cultures | | |
|---|---|---|
| | P3X63Ag8 | F5-a-1/22.8.13 |
| R-α IgG1 | + | − |
| R-α IgG2a | − | − |
| R-α IgG2b | − | − |
| R-α IgG3 | − | − |
| R-α K chain | + | + |
| R-α λ chain | − | − |
| R-α IgM | − | + |

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the present specification and examples, the present invention is industrially useful in several respects. Although this prostate antigen is an eutopic product, it appears to be a useful tumor marker such as other differentiated cell products, e.g., prostatic acid phosphatase and thyrocalcitonin. The specificity of prostate antigen antiserum can allow for the identification of neoplastic cells in isolated metastases with unknown primary origin. Anti-prostate antigen antiserum can also be used as a vector to localize and/or carry cytotoxic substances to neoplastic prostatic tissue. Further, the study of variations in the expression of normal differentiation between antigens of prostatic tissue during development of the gland and in prostatic lesions can provide insight into the phenomenon of growth regulation and metastatic ability of prostate cells.

What is claimed is:

1. An in vivo composition of matter comprising an immunochemically effective concentration and amount of a purified human prostate specific antigen occurring in normal and cancerous prostatic tissue and purified to show a single protein band on analytical polyacrylamide gel electrophoresis and isoelectric focusing, said antigen having a molecular weight as determined by Sephadex G-75 gel of filtration of about 33,000 and by a molecular weight as determined by sodium dodecyl sulfate polyacrylamide gel electrophoresis of about 34,000 with no subunit and having an isoelectric point pI of 6.9, said antigen further being insoluble in perchloric acid and substantially free of normal serum protein components, water-insoluble cellular material and of prostatic acid phosphatases.

2. An in vitro composition of matter comprising an immunochemically effective concentration and amount of antibodies against a human prostate specific antigen occurring in normal and cancerous prostatic tissue and purified to show a single protein band on analytical polyacrylamide gel electrophoresis and isoelectric focusing, said antigen having a molecular weight by Sephadex G-75 gel filtration of about 33,000 and by sodium dodecyl sulfate polyacrylamide gel electrophoresis of about 34,000 with no subunit and having an isoelectric point pI of 6.9, said antigen further being insoluble in perchloric acid and said composition being free of antibodies against humen prostatic acid phosphatases.

3. A composition according to claim 2, wherein said antibodies are monoclonal antibodies.

4. A composition according to claim 2, wherein said antibodies are immunoprecipitating antibodies.

5. A composition according to claim 2, wherein said antibodies are labeled for radioimmunoassay or enzyme-linked immunoassay.

6. A composition according to claim 2, wherein said antibodies are covalently bonded to a water-insoluble support.

7. A process for preparing immunoprecipitating antibodies to antigens associated with prostatic tissue and fluid, which comprises:

(a) extracting an antigen according to claim 1 from prostatic tissue or separating said antigen from prostatic fluid;
(b) separating said antigen from extraneous antigenic proteins to obtain a composition consisting essentially of said antigen;
(c) immunizing animals with the resultant purified antigen to form antibodies specific thereto; and
(d) recovering immunoprecipitating antibodies against said antigen from said animals.

8. A process according to claim 7, wherein said antigen is separated from extraneous antigenic protein material by salting out.

9. A process according to claim 7, wherein said antigen is obtained from seminal fluid.

10. A process preparing antibodies to antigens associated with prostatic tissue and fluid, which comprises:

(a) cloning hybridoma cells capable of secreting said antibodies;
(b) extracting antibodies according to claim 2 from said secretions;
(c) separating said antibodies from extraneous antigenic proteins to obtain a composition consisting essentially of said antibodies; and
(d) recovering an immunologically effective concentration and amount of said antibodies from said cells.

11. A process according to claim 10, wherein said hybridoma cells are prepared by fusing a nonsecretory myeloma cell line with primary mouse spleen cells.

12. A method for diagnosing carcinoma of the prostate, which comprises:

(a) forming an immunoprecipitin complex between (i) an an antigen consisting essentially of the human prostate specific antigen of claim 1 associated with both normal and cancerous prostatic tissue which is distinct from prostatic acid phosphatase and (ii) immunoprecipitating antibodies thereto which are free of cross-reactivity against prostatic acid phosphatases and against antigens associated with other carcinomas; and (b) detecting the presence of said complex.

13. A method according to claim 12, wherein the complex is formed by countercurrent immunoelectrophoresis.

14. A method according to claim 12, wherein the complex is formed by immunologically reacting said antigen with antibodies thereto covalently bound to a water-insoluble carrier.

15. A method according to claim 12, wherein said complex is detected by radioimmunoassay or by enzyme-linked immunoassay.

16. A continuous murine cell line capable of producing monoclonal antibodies of the IgM isotype to the specific antigen of claim 1 under nutrient growth conditions, consisting essentially of a fused cell hybrid of:

(a) primed antibody-producing cells with (b) myeloma cells capable of producing a homogeneous population of immunoglobulin in the fused hybridoma.

17. A cell line according to claim 16, wherein the fused cell hybrid is ATCC HB 8051.

*18. A method for diagnosing carcinoma of the prostate, which comprises:*

*(a) contacting a body fluid selected from the group consisting of blood, a blood fraction, and urine of a human being with immunoprecipitating antibodies to an antigen consisting essentially of the human prostate specific antigen of claim 1 associated with both normal and cancerous prostatic tissue which is distinct from prostatic acid phosphatase, said antibodies being free of cross-reactivity against prostatic acid phosphatases and against antigens associated with other carcinomas to form an immunoprecipitin complex between said antibodies and said antigen; and*

*(b) detecting the presence of said complex.*

*19. The method according to claim 18 in which the body fluid is blood.*

*20. The method according to claim 18 in which the body fluid is a blood fraction.*

*21. The method according to claim 18 in which the body fluid is serum.*

*22. The method according to claim 18 in which the body fluid is urine.*

*23. The method according to claim 18 in which the antibodies are monoclonal antibodies.*

*24. The method according to claim 18 wherein the complex is formed by countercurrent immunoelectrophoresis.*

*25. The method according to claim 18 wherein the complex is formed by immunologically reacting said antigen with antibodies thereto covalently bound to a water-insoluble carrier.*

*26. The method according to claim 18, wherein said complex is detected by radioimmunoassay or by enzyme-linked immunoassay.*

*27. The method according to claim 12 wherein the antigen is localized in a human tissue sample.*

*28. The method according to claim 33 in which the antibodies are monoclonal antibodies.*

*29. The method according to claim 33 wherein the complex is formed by countercurrent immunoelectrophoresis.*

*30. The method according to claim 33 wherein the complex is formed by immunologically reacting said antigen with antibodies thereto covalently bound to a water-insoluble carrier.*

*31. The method according to claim 33 wherein said complex is detected by radioimmunoassay or by enzyme-linked immunoassay.*

*32. The method according to claim 33 in which the tissue is prostatic tissue.*

* * * * *

UNITED STATES PATENT AND TRADEMARK OFFICE

CERTIFICATE OF CORRECTION

PATENT NO. : Re. 33,405

DATED : October 23, 1990

INVENTOR(S) : T. Ming Chu, et al.

It is certified that error appears in the above-identified patent and that said Letters Patent is hereby corrected as shown below:

On the Title page, Section [73]: "Tuscon" should read as --Tucson--

Column 3, line 9: delete "in"

Column 3, line 11: "detectable" should read as --detectable in--

Column 3, line 47: "monitorong" should read as --monitoring--

Column 3, line 62: delete "a"

Column 4, line 23: "a" should read as --the--

Column 4, line 47: "that" should read as --the--

Column 5, line 42: "theis" should read as --this--

Column 5, line 61: "Thus" should read as --This--

Column 6, lines 51-52: "immunodifusion" should read as --immunodiffusion--

Column 6, line 61: "hypertropic" should read as --hypertrophic--

Column 11, line 47: "264-165" should read as --264-265--

Column 13, line 17: "slaine" should read as --saline--

Column 13, line 39: "2.5 + 20" should read as --2.5 X 20--

Column 15, line 33: "pancrease" should read as --pancreas--

Column 15, line 48: "hypertropic" should read as --hypertrophic--

Column 16, line 39: "hypertropic" should read as --hypertrophic--

Column 17, line 51: "pancrease" should read as --pancreas--

Column 18, line 17: "applied" should read as --added--

UNITED STATES PATENT AND TRADEMARK OFFICE

CERTIFICATE OF CORRECTION

PATENT NO. : Re. 33,405

DATED : October 23, 1990

INVENTOR(S) : T. Ming Chu, et al.

It is certified that error appears in the above-identified patent and that said Letters Patent is hereby corrected as shown below:

Column 18, line 51: "actate" should read as --acetate--

Column 19, line 22: "HT-20" should read as --HT-29--

Column 19, line 54: "dehydrogenasde" should read as --dehydrogenase--

Column 23, line 9: "absorbing" should read as --adsorbing--

Column 25, line 63: "gel of filtration" should read as --gel filtration--

Column 25, line 63: delete "by"

Column 26, line 15: "humen" should read as --human--

Column 28, line 23, Claim 28: "claim 33" should read as --claim 27--

Column 28, line 25, Claim 29: "claim 33" should read as --claim 27--

Column 28, line 27, Claim 30: "claim 33" should read as --claim 27--

Column 28, line 31, Claim 31: "claim 33" should read as --claim 27--

UNITED STATES PATENT AND TRADEMARK OFFICE

CERTIFICATE OF CORRECTION

PATENT NO. : Re. 33,405

DATED : October 23, 1990

INVENTOR(S) : T. Ming Chu, et al.

It is certified that error appears in the above-identified patent and that said Letters Patent is hereby corrected as shown below:

Column 28, line 34, Claim 32: "claim 33" should read as --claim 27--

Signed and Sealed this

Seventeenth Day of March, 1992

*Attest:*

HARRY F. MANBECK, JR.

*Attesting Officer*

*Commissioner of Patents and Trademarks*